United States Patent [19]

Kéri et al.

[11] Patent Number: 4,702,915

[45] Date of Patent: Oct. 27, 1987

[54] SKIN REGENERATING COSMETIC COMPOSITION

[75] Inventors: Tibor Kéri; Jánosné Kristóf, both of Debrecen, Hungary

[73] Assignee: Innofinance Altalanos Innovacios Penzintezet, Budapest, Hungary

[21] Appl. No.: 890,777

[22] PCT Filed: May 29, 1985

[86] PCT No.: PCT/HU85/00065

§ 371 Date: Jul. 1, 1986

§ 102(e) Date: Jul. 1, 1986

[87] PCT Pub. No.: WO86/02833

PCT Pub. Date: May 22, 1986

[30] Foreign Application Priority Data

Nov. 12, 1984 [HU] Hungary ............................ 4194/84
Oct. 9, 1985 [HU] Hungary ............................ 4194/84

[51] Int. Cl.$^4$ ............................................. A61K 35/78
[52] U.S. Cl. ..................................... 424/195.1; 514/844
[58] Field of Search ...................... 424/195.1; 514/844

[56] References Cited

FOREIGN PATENT DOCUMENTS

| 1492023 | 2/1969 | Fed. Rep. of Germany . |
| 1492118 | 7/1969 | Fed. Rep. of Germany . |
| 1492148 | 9/1969 | Fed. Rep. of Germany . |
| 1617365 | 4/1971 | Fed. Rep. of Germany . |
| 1767098 | 4/1972 | Fed. Rep. of Germany . |
| 2232733 | 7/1974 | Fed. Rep. of Germany . |
| 2052080 | 3/1971 | France . |

OTHER PUBLICATIONS

Remington, Practice of Pharmacy, 795–797, 1985.
Hagers Handbuch der Pharmazeutischen Praxis, List, P. H. et al., p. 559, (Springer-Verlag 1977).
Lexikon der Kosmetischen Praxis, Volk, R. et al., pp. 560–563 and 78–79 (1936).

*Primary Examiner*—J. R. Brown
*Assistant Examiner*—John W. Rollins, Jr.
*Attorney, Agent, or Firm*—Karl F. Ross; Herbert Dubno

[57] ABSTRACT

The invention is concerned with a skin regenerating cosmetic composition which contains as active ingredient the extract of the pod and/or grain of green peas.

9 Claims, No Drawings

SKIN REGENERATING COSMETIC COMPOSITION

The invention relates to a skin regenerating cosmetic composition.

BACKGROUND OF THE INVENTION

There are many excellent compositions on the cosmetic market, the great part of which is based on synthetic elements. The skin regenerating compositions mainly due to their fat and water content improve the condition of the skin. Recently also the use of active ingredients of plant origin is discussed. Because of the great variety of the active ingredients of plant origin only the following are mentioned as examples: grape, palm, fruit of the cocoa tree, gingko leaf (German Patent specifications Nos. 1,492,023, 1,492,118, 1,492,148, 1,617,365, 1,767,098 and 2,232,733). But the plant residues obtained during the processing of agricultural cultivated plants and mainly waste in the preserves industry have not been examined in view of their applicability in the cosmetic industry.

The aim of the present invention was to find new active ingredients of plant origin for use in the cosmetic industry.

Another aim of the present invention was to find plant parts obtained as waste during the processing of agricultural cultivated plants which can be used as active ingredients in cosmetic compositions.

BRIEF DESCRIPTION OF THE INVENTION

During our experiments it has been surprisingly found that by the extraction of the pod and/or grain of green peas an active ingredient, a solution was obtained which was excellently suitable for calming the inflamed skin, improving the scarfskin formation of wounded skin, for light protection, for treating pustules or other inflamatory formations when admixed in a suitable ratio with diluents and/or vehicles and optionally other known substances used in the cosmetic industry, e.g. propolis.

DETAILED DESCRIPTION OF THE INVENTION

The present invention relates to skin regenerating cosmetic compositions comprising the extract of the pod and/or grain of green peas as active ingredient together with the usual vehicles and/or diluents.

The extract is prepared from the pod and/or grain of green peas with water or with a mixture of water and a water miscible organic solvent, preferably with the mixture of ethanol and water by steeping or boiling. After filtering the extract the solution of the active ingredient is formulated directly or after lyophilization with the usual cosmetic vehicles and/or diluents.

The composition of the invention shows a very favorable effect.

The face lotion (Example 7) was examined on 45 women aged from 20 to 65 years. The cream was applied after thorough cleaning twice a day, in the morning and evening. The treatment was continued for two weeks. The following types of face skin were examined: 35 slightly dry, 9 sensitive, dry, 1 very dry skin. The cream has been absorbed well during the treatment, the skin became smooth, velvety. During the treatment no allergic reaction, irritative dermatitis or hypersensitivity were observed.

The body lotion (Example 9) was tested on 32 women aged from 17 to 68 years. The composition was applied after thorough washing twice daily, in the morning and evening. The treatment was continued for two weeks. The following types of skin were examined: 2 normal sensitive, 4 dry sensitive, 18 dry and 8 normal skins. The composition has been absorbed well during each treatment, the skin became velvety, smooth, the skin tightening and dryness which occurred after washing (having a bath or shower) stopped and the skin was calmed and refreshed. No allergic reaction, irritative dermatitis or hypersensitivity was observed.

The following non-limiting Examples show the compositions of the invention and the preparation of the active ingredient.

EXAMPLE 1

Pods of green peas deprived of their grains were dried at room temperature in a manner usual for herbs, then crushed. 1 kg of the crushed substance was suspended in 4.00 liters of water and steeped in a dry, cool place for 24 hours. After filtration the solution was boiled, then a 20% by vol. solution was prepared with cosmetic vaseline oil. The solution was stored in a dry, cool, dark place until use.

EXAMPLE 2

Pods of green peas deprived of their grains were dried as in Example 1 then powdered. 4.5 liters of deionized water were added to 1 kg of the powdered substance. The mixture was boiled for 2 hours, the resulting solution was filtered and closed hermetically until use. It was stored in a dark, cool, dry place.

EXAMPLE 3

Pods of green peas deprived of their grains were dried as in Example 1 then powdered. 4.10 liters of 70% by vol. of aqueous ethanol were added to 1 kg of the powdered substance. The substance was steeped for 72 hours, then the solution was filtered and after having been covered it was stored in a dry, cool, dark place.

EXAMPLE 4

Pods of green peas deprived of their grains were dried as in Example 1 then powdered. 5 liters of deionized water were added to 1 kg of the powdered substance. The substance was steeped for 32 hours. After filtration the solution was boiled, then it was stored in a dry, cool, dark place until use.

EXAMPLE 5

Pods of green peas deprived of their grains which were obtained in the preserves industry were crushed, then diluted with water to 4-fold volume and steeped for 36 hours. After filtration the solution was boiled, then stored in dry, cool, dark place.

EXAMPLE 6

1 kg of grains of green peas was ground and steeped in 5 liters of deionized water for 30 hours. After filtration the solution was boiled, then it was stored in dry, cool, dark place until use.

EXAMPLE 7

1 kg of grains of green peas was ground and dried as in Example 1 then it was powdered. 4.5 liters of 70% by vol. of ethanol were added to 1 kg of the powdered substance, then the substance was steeped for 36 hours, the solution was dried and lyophilized.

EXAMPLE 8

4.0 liters of deionized water were added to 1 kg of dried and powdered grain of green peas, the mixture was boiled for 2 hours, the solution was filtered and stored in a dry, cool, dark place until use.

EXAMPLE 9

The wet mixture of grains and pods of green peas obtained in the preserves industry was dried as in Example 1 then 1 kg of the dried mixture was steeped in 4.5 liters of deionized water for 36 hours. After filtration the solution was lyophilized.

EXAMPLE 10

3 kg of grain of green peas and 1 kg of pod of green peas were ground together then the mixture was dried as in Example 1. 1 kg of the dried mixture was boiled in 5 liters of deionized water for 3 hours. After filtration the product was covered and stored in a dark, cool, dry place.

EXAMPLE 11

Skin regenerating body lotion

| Components | % by weight |
| --- | --- |
| Extract of Example 2 | 18.00 |
| cetyl alcohol | 1.83 |
| stearin | 4.70 |
| vaseline oil (cosmetic quality) | 2.33 |
| castor oil | 1.83 |
| sodium laurylsulfate | 1.17 |
| sorbitol | 3.60 |
| glycerol | 6.00 |
| Nipagine | 0.20 |
| tocopherol acetate | 0.05 |
| perfume oil | 0.10 |
| deionized water | 60.19 |

EXAMPLE 12

Skin regenerating face lotion

| Components | % by weight |
| --- | --- |
| Extract of Example 3 | 18.00 |
| cetyl alcohol | 1.50 |
| stearin | 4.50 |
| vaseline oil (cosmetic quality) | 2.50 |
| castor oil | 2.00 |
| vaseline MD | 0.80 |
| sodium laurylsulfate | 1.17 |
| sorbitol | 3.70 |
| glycerol | 6.00 |
| Nipagine | 0.20 |
| tocopherol acetate | 0.05 |
| perfume oil | 0.10 |
| deionized water | 59.48 |

EXAMPLE 13

Skin regenerating composition for hand treatment

| Components | % by weight |
| --- | --- |
| Extract of Example 5 | 18.00 |
| cetyl alcohol | 6.40 |
| stearin | 2.80 |
| vaseline MD | 2.80 |
| vaseline oil (cosmetic quality) | 2.80 |

-continued

| Components | % by weight |
| --- | --- |
| castor oil | 0.30 |
| glycerol monostearate | 0.50 |
| lanoline | 3.00 |
| sodium laurylsulfate | 0.83 |
| sorbitol | 3.00 |
| glycerol | 4.73 |
| propylene glycol | 2.00 |
| Nipagine | 0.20 |
| tocopherol acetate | 0.07 |
| vitamin A | 0.01 |
| vitamin K-III | 0.05 |
| perfume oil | 0.13 |
| propolis | 0.11 |
| deionized water | 52.27 |

EXAMPLE 14

Skin regenerating and hydrating lotion for shower

| Components | % by weight |
| --- | --- |
| Extract of Example 2 | 20.00 |
| Hostapur SAS (Hoechst AG) | 20.0 |
| Genapol AMS (Hoechst AG) | 40.0 |
| betain | 10.0 |
| Genapol PMS | 2.0 |
| maize oil | 2.0 |
| perfume substance | 0.6 |
| deionized water | 5.4 |

EXAMPLE 15

Skin regenerating and hydrating shampoo

| Components | % by weight |
| --- | --- |
| Extract of Example 6 | 37.0 |
| Genapol ZRO (Hoechst AG) | 35.0 |
| Genapol AMS (Hoechst AG) | 10.0 |
| betain | 8.0 |
| coco-fatty acid diethanolamide | 2.0 |
| sodium chloride | 1.4 |
| perfume substance | 0.2 |
| distilled water | 6.4 |

EXAMPLE 16

Skin regenerating and hydrating tonic

| Components | % by weight |
| --- | --- |
| Extract of Example 3 | 28.00 |
| retinoin acid | 0.05 |
| ethanol (96%) | 61.25 |
| propylene glycol | 10.00 |
| Tween 20 | 0.50 |
| perfume substance | 0.20 |

EXAMPLE 17

Skin regenerating and hydrating liquid soap

| Components | % by weight |
| --- | --- |
| Lyophilisate of Example 9 | 3.7 |
| Genapol TSM (Hoechst AG) | 3.0 |
| Genapol LRO (Hoechst AG) | 35.0 |
| Medilan KA (Hoechst AG) | 8.0 |
| sodium chloride | 1.3 |
| distilled water | 48.8 |

| Components | % by weight |
| --- | --- |
| perfume substance | 0.2 |

EXAMPLE 18

Skin regenerating and hydrating face cleaning emulsion

| Components | % by weight |
| --- | --- |
| Extract of Example 8 | 35.0 |
| Hostaphat KL 340N (Hoechst AG) | 2.0 |
| Hostacerin DGS (Hoechst AG) | 4.0 |
| Hostacerin PN 73 (Hoechst AG) | 0.6 |
| paraffine oil | 5.0 |
| isopropyl palmitate | 6.0 |
| propylene glycol | 3.0 |
| distilled water | 44.2 |
| perfume substance | 0.2 |

EXAMPLE 19

Body powder 4.25 g of the lyophilisate of Example 9 were mixed with 95.5 g of talc and 0.25 g of menthol. The product was sterilized by UV radiation.

EXAMPLE 20

Skin regenerating body lotion

The composition is the same as in Example 11 wherein the 18.00% by weight extract of the active ingredient can be prepared according to any of Examples 1 to 10.

EXAMPLE 21

Skin regenerating face lotion

The composition is the same as in Example 12 wherein the 18.00% by weight extract of the active ingredient can be prepared according to any of Examples 1 to 10.

EXAMPLE 22

Skin regenerating composition for hand treatment

The composition is the same as in Example 13 wherein the 18.00% by weight extract of the active ingredient can be prepared according to any of Examples 1 to 10.

We claim:

1. A process for the preparation of a skin-regenerating cosmetic composition which comprises the steps of:
    (a) crushing green pea grain or green pea pod;
    (b) extracting the crushed green pea grain or green pea pod with water or with a mixture of water and ethanol to form an extract containing a cosmetically active ingredient;
    (c) filtering the extract obtained during step (b) to provide a solution containing the cosmetically active ingredient; and
    (d) combining the solution containing the cosmetically active ingredient with a cosmetically acceptable vehicle or diluent.

2. The process defined in claim 1 wherein prior to step (2) the green pea grain or green pea pod is dried at room temperature.

3. The process defined in claim 1 wherein in step (a) the green pea grain or green pea pod is crushed to a powder.

4. The process defined in claim 1 wherein during step (b) the crushed green pea grain or green pea pod is extracted by steeping.

5. The process defined in claim 1 wherein during step (b) the crushed green pea grain or green pea pod is extracted by boiling.

6. The process defined in claim 1 wherein following step (c) the solution containing the active ingredient is boiled.

7. The process defined in claim 1 wherein following step (c) the solution containing the active ingredient is lyophilized.

8. The skin-regenerating cosmetic composition prepared by the process defined in claim 1.

9. A method of cosmetically improving the skin in order to provide skin-regeneration which comprises the step of directly applying to an inflamed area of skin, a cosmetically effective amount of the skin-regenerating composition defined in claim 8.

* * * * *